(12) United States Patent
Botma et al.

(10) Patent No.: US 10,495,655 B2
(45) Date of Patent: *Dec. 3, 2019

(54) AUTOMATED SELECTION OF MICROORGANISMS AND IDENTIFICATION USING MALDI

(71) Applicant: BD KIESTRA B.V., Drachten (NL)

(72) Inventors: Jetze Botma, Drachster Compagnie (NL); Martijn Kleefstra, Surhuisterveen (NL); Tino Walter Van der Zee, Wiuwert (NL)

(73) Assignee: BD KIESTRA B.V., Drachten (NL)

( * ) Notice: Subject to any disclaimer, the term of this patent is extended or adjusted under 35 U.S.C. 154(b) by 0 days.

This patent is subject to a terminal disclaimer.

(21) Appl. No.: 16/058,414

(22) Filed: Aug. 8, 2018

(65) Prior Publication Data

US 2018/0364264 A1    Dec. 20, 2018

Related U.S. Application Data

(63) Continuation of application No. 15/663,540, filed on Jul. 28, 2017, now Pat. No. 10,073,105, which is a continuation of application No. 15/383,573, filed on Dec. 19, 2016, now Pat. No. 9,753,045, which is a continuation of application No. 14/388,430, filed as application No. PCT/NL2013/050239 on Apr. 2, 2013, now Pat. No. 9,556,495.

(60) Provisional application No. 61/618,003, filed on Mar. 30, 2012.

(51) Int. Cl.
| | |
|---|---|
| *G01N 35/00* | (2006.01) |
| *G01N 35/10* | (2006.01) |
| *H01J 49/16* | (2006.01) |
| *C12M 1/22* | (2006.01) |
| *C12M 1/26* | (2006.01) |
| *C12M 1/36* | (2006.01) |
| *C12Q 3/00* | (2006.01) |
| *G01N 1/04* | (2006.01) |

(52) U.S. Cl.
CPC ....... *G01N 35/00029* (2013.01); *C12M 23/10* (2013.01); *C12M 33/04* (2013.01); *C12M 41/48* (2013.01); *C12Q 3/00* (2013.01); *G01N 35/10* (2013.01); *H01J 49/164* (2013.01); *G01N 2001/045* (2013.01); *G01N 2035/1032* (2013.01)

(58) Field of Classification Search
CPC .............................................. G01N 35/00029
See application file for complete search history.

(56) References Cited

U.S. PATENT DOCUMENTS

| | | | |
|---|---|---|---|
| 2,315,329 A | 3/1943 | Hood et al. | |
| 4,617,265 A | 10/1986 | Peterson | |
| 5,432,085 A | 7/1995 | Warren et al. | |
| 5,808,300 A | 9/1998 | Caprioli | |
| 6,787,764 B2 | 9/2004 | Park | |
| 6,875,616 B1 | 4/2005 | Forssmann et al. | |
| 7,166,441 B2 | 1/2007 | Nadler et al. | |
| 7,978,258 B2 | 7/2011 | Christiansen et al. | |
| 8,058,078 B2 | 10/2011 | Hansen et al. | |
| 8,412,464 B1 | 4/2013 | Wick et al. | |
| 8,450,081 B2 | 5/2013 | Weller | |
| 8,835,176 B2 | 9/2014 | Boβmeyer et al. | |
| 8,877,459 B2 | 11/2014 | Weller | |
| 9,121,005 B2 | 9/2015 | Van Der Kaap et al. | |
| 9,121,794 B2 | 9/2015 | Vossgroene | |
| 9,171,709 B2 | 10/2015 | Lasch et al. | |
| 9,180,448 B2 | 11/2015 | Armstrong et al. | |
| 9,556,495 B2 * | 1/2017 | Botma | G01N 35/00029 |
| 9,753,045 B2 * | 9/2017 | Botma | G01N 35/00029 |

(Continued)

FOREIGN PATENT DOCUMENTS

| | | |
|---|---|---|
| CN | 101099683 A1 | 1/2008 |
| CN | 101646763 A | 2/2010 |

(Continued)

OTHER PUBLICATIONS

Office Action issued in CN Application No. 2017104178219 dated Mar. 5, 2018.
European Search Report received in EP application No. 17182362.8 dated Nov. 29, 2017, pp. 10.
""Micronaut ASTroID", F-_ASTroiD_01072011_01_e_CH", Merlin Diagnostika GmbH, (Jul. 1, 2011), pp. 1-2.
"International Search Report for Application No. PCT/NL2013/050239", (dated Nov. 22, 2013).
"Office Action issue in corresponding Russian Application No. 2014143720", (dated Mar. 23, 2017).

(Continued)

*Primary Examiner* — Albert M Navarro
(74) *Attorney, Agent, or Firm* — Botos Churchill IP Law LLP (57) ABSTRACT

A method and apparatus for locating and selecting a colony of microorganisms on a culture dish and identifying microorganisms in said selected colony using MALDI. The method comprises the automated steps of locating and selecting a colony of microorganisms on a culture dish; obtaining a sample of said selected colony of microorganisms; depositing at least some of said sample of said selected colony of microorganisms on a target plate; and transferring said target plate with said sample in an apparatus for performing MALDI for identification of said sample of said selected colony of microorganisms. A sample of a colony of microorganisms is automatically deposited on a depositing spot such that the sample covers at most approximately half of said one of the depositing spots of the target plate. A suspension of a sample of microorganisms is automatically prepared by automatically picking the sample with a picking tool and submerging the picking tool with said sample in a suspension, after which the picking tool is vibrated in vertical sense only to release the sample from the picking tool.

20 Claims, 1 Drawing Sheet

(56) References Cited

U.S. PATENT DOCUMENTS

| | | | |
|---|---|---|---|
| 10,073,105 | B2* | 9/2018 | Botma ............. G01N 35/00029 |
| 2002/0016450 | A1 | 2/2002 | Laugham et al. |
| 2002/0155445 | A1 | 10/2002 | Jarvik |
| 2004/0185521 | A1 | 9/2004 | Yoshida et al. |
| 2004/0267181 | A1 | 12/2004 | Tuite et al. |
| 2006/0194715 | A1 | 8/2006 | Blackburn et al. |
| 2007/0196817 | A1 | 8/2007 | Broom |
| 2007/0218564 | A1 | 9/2007 | Bachmann et al. |
| 2008/0286757 | A1 | 11/2008 | Gaisford et al. |
| 2009/0061183 | A1 | 3/2009 | Muraguchi et al. |
| 2009/0116714 | A1 | 5/2009 | Richmond et al. |
| 2009/0131524 | A1 | 5/2009 | Gibson et al. |
| 2009/0197284 | A1 | 8/2009 | Kiernan et al. |
| 2010/0074507 | A1 | 3/2010 | Klottrup et al. |
| 2010/0112722 | A1 | 5/2010 | Mrksich et al. |
| 2010/0116980 | A1 | 5/2010 | Nassif et al. |
| 2010/0209293 | A1 | 8/2010 | Ikawa et al. |
| 2010/0227414 | A1 | 9/2010 | Ervin |
| 2010/0323917 | A1 | 12/2010 | Vertes et al. |
| 2011/0009473 | A1 | 1/2011 | Tong et al. |
| 2012/0009558 | A1 | 1/2012 | Armstrong et al. |
| 2012/0028238 | A1 | 2/2012 | Richmond et al. |
| 2012/0152041 | A1 | 6/2012 | Maier |
| 2012/0277905 | A1 | 11/2012 | Botma et al. |
| 2013/0109047 | A1 | 5/2013 | Charrier et al. |
| 2013/0182648 | A1 | 7/2013 | Abe et al. |
| 2013/0302847 | A1 | 11/2013 | Mix |
| 2013/0337502 | A1 | 12/2013 | Bo Meyer et al. |
| 2014/0227723 | A1 | 8/2014 | Ingber et al. |
| 2015/0004644 | A1 | 1/2015 | Vandenesch et al. |

FOREIGN PATENT DOCUMENTS

| | | |
|---|---|---|
| DE | 10013513 A1 | 10/2000 |
| DE | 102004020885 | 11/2015 |
| EA | 001033 B1 | 8/2000 |
| GB | 2315329 A1 | 1/1998 |
| JP | 2000157257 A | 6/2000 |
| JP | 2000171360 A | 6/2000 |
| JP | 2004305062 A | 11/2004 |
| JP | 2009508490 A | 3/2009 |
| JP | 2011254806 A | 12/2011 |
| JP | 2012073197 A | 4/2012 |
| WO | 20090061183 A1 | 5/2009 |
| WO | 2011055791 A1 | 12/2011 |
| WO | 2012004545 A1 | 1/2012 |
| WO | 2013182648 A1 | 12/2013 |

OTHER PUBLICATIONS

"Third Party Observations for EP Application No. 13717580.8", Received from European Patent Office, (dated Aug. 30, 2016).

Bean, H D, et al., "Bacterial volatile discovery using solid phase microextraction and comprehensive two dimensional gas chromatography lime of flight mass spectrometry", Journal of Chromatography B, vol. 901, (2012), pp. 41-46.

Bruker , et al., ""Bruker and KIESTRA Lab Automation Announce Alliance in Microbial Identification by MALDI Biotyper Molecular Fingerprinting and Microbiology Lab Automation"", Bruker Daltonics,, (Sep. 4, 2010), pp. 1-2.

Dell, H. , ""Automated Colony Pickers Evolve", article No. 16574", The Scientist Magazine®, (Jul. 4, 2005), pp. 1-5.

Junkins , et al., "Comparison of BD Phoenix AP workflow with Vitek 2", Journal of Clinical Microbiology,, vol. 48, No. 5, (May, 2010), pp. 1929-1931.

Lange, Oliver , et al., "MIROB: automatic rapid identification of micro-organisms in high through-put", Industrial Robot: An International Journal, vol. 35(4), (2008), pp. 311-315.

Maquelin, Kees , et al., "Raman Spectroscopic Method for Identification of Clinically Relevant Microorganisms . . . ", Anal. Chem.; vol. 72, (2000), pp. 12-19.

Tait, Emma , et al., "Identification of volatile Organic compounds produced by Bacteria using HS-SPME-GC-MS", Journal of Chromatographic Science, vol. 52, (2014), pp. 363-373.

Van Veen, S O, et al., "High-Throughput Identification of Bacteria and Yeast by Matrix-Assisted Laser . . . ", Journal of Clinical Microbiology, vol. 48(3), (Mar. 2010), pp. 900-907.

* cited by examiner

AUTOMATED SELECTION OF MICROORGANISMS AND IDENTIFICATION USING MALDI

CROSS-REFERENCE TO RELATED APPLICATIONS

The present application is a continuation of U.S. patent application Ser. No. 15/663,540, filed on Jul. 28, 2017, which is a continuation of U.S. patent application Ser. No. 15/383,573, filed on Dec. 19, 2016, now U.S. Pat. No. 9,753,045, issued on Sep. 5, 2017, which is a continuation of U.S. patent application Ser. No. 14/388,430, filed on Sep. 26, 2014, now U.S. Pat. No. 9,556,495, issued on Jan. 31, 2017, which is a national phase entry under 35 U.S.C. § 371 of International Application No. PCT/NL2013/050239 filed Apr. 2, 2013, published in English, which claims priority from U.S. Provisional Patent Application No. 61/618,003, filed Mar. 30, 2012, all of which are incorporated herein by reference.

BACKGROUND OF THE INVENTION

The present invention generally relates to a method for locating and selecting a colony of microorganisms and identifying microorganisms using MALDI, in particular MALDI-TOF-MS (Matrix Assisted Laser Desorption and Ionization Time-of-Flight Mass Spectroscopy) and the systems for performing such methods.

MALDI-analysis is a useful tool for solving structural problems in biochemistry, immunology, genetics and biology. Samples are ionized in the gas phase and a time of flight (TOF) analyzer is used to measure ion masses. TOF analysis begins when ions are formed and are accelerated to a constant kinetic energy as they enter a drift region. They arrive at a detector following flight times that are proportional to the square root of their masses. A mass spectrum is created because ions of different mass arrive at the detector at different times.

Mass spectrometry can be a powerful tool in the fields of drug discovery and development, genotyping, and proteome research. In addition MALDI has already been used for characterization and identification of bacteria and microorganisms. Current trends in research are to analyze larger and larger numbers of samples using quantities of individual samples ranging from the micro-mole levels to ato-mole levels. As a result, samples are also becoming smaller and needs exists for efficient and reliable acquisition of the correct amount of micro-organisms and accurately depositing a sample of the acquired amount on a target plate used in the MALDI-instrument.

In a typical MALDI TOF MS operation, the sample to be analyzed is spotted or deposited on a metal plate (also called target plate or MALDI-plate), reagents are added (matrix) that support ionization, and then they are dried to form crystals. In these instruments, the target plate is positioned in a fixed position in the MALDI-instrument. The target plate has a plurality of depositing spots (e.g. from 24 to 384 depositing spots on a single target plate) and these depositing spots have a fixed orientation with regard to the edges of the target plate. The target plate is positioned on an X-Y stage so that an obtained sample of a colony of microorganisms can be deposited on a selected depositing spot. A high voltage potential is maintained between the target plate and a metal grid. This voltage can be maintained or pulsed, depending upon the desired results and a vacuum is created in the chamber. A laser is fired into the sample/matrix and a plume of ions is formed. The voltage difference is used to accelerate the ions up a flight tube so that they can be analyzed. The analysis directly relates the time of flight to the mass of the ionized component.

Several parameters can affect the quality of the results, including flatness of the target, amount and type of matrix, concentration of the sample, conductivity of the sample target, accuracy of placement on the depositing spot, as well as other variables.

In particular, an important aspect is the handling of the sample and the concentration of the sample. It is known that a suspension is made from a sample of a colony of microorganisms and that a researcher pipettes a drop of the obtained suspension containing the sample onto a depositing spot of the target plate by hand. To provide a correct analysis, however, the suspension has to contain a sufficient concentration of the sample from the start.

In preparing such a suspension of a sample of microorganisms, a handheld device comprising a drive. The drive comprises a housing with a rotary drive motor contained therein, and a connector which is configured for the releasable attachment of the sample acquisition device to the drive. The sample acquisition device comprises a sample collection region which is first brought into contact with biological material (mostly grown on a culture dish) to be analyzed. Thereafter the sample collection region is attached to the rotary drive, brought into contact with a liquid medium contained in a tube and the rotary drive is activated for a certain period of time such that a sample of the biological material in the sample acquisition device is released in the liquid medium. After the sample collection region is removed from the tube the suspension tube holds a suspension containing the sample which for example can be used for performing MALDI-analysis.

However, the efficiency of release of the sample from the sample acquisition region can in some cases be insufficient to perform a correct analysis of the microorganism suspended in the liquid medium. This may result in a prepared suspension that is unusable, resulting in lost of time and money. In addition since the sample collection region is rotated within the tube the tube must be of a sufficient dimension to allow such rotation without the sample acquisition region contacting the inner wall of the tube which might be detrimental for the release of the microorganism in the liquid medium. Such a relative large dimensioned tube thus contains a relatively large volume of liquid medium, leading to a corresponding lengthy time of further processing such liquid suspension medium. For example, the time in which the liquid suspension containing the sample has to incubate in an incubator is proportional to the amount of suspension liquid. Therefore, there is a need for a method in which the preparation of a suspension of a sample of microorganisms is performed automatically leading to a much more reproducible manner of preparing such a suspension. In addition there is a need for reliably and reproducibly releasing the sample on a depositing spot of a target plate.

BRIEF SUMMARY OF THE INVENTION

In order to solve at least one of the problems mentioned above the present invention provides a method for locating and selecting a colony of microorganisms on a culture dish and identifying microorganisms in said selected colony using MALDI, wherein said method comprises the automated steps of: locating and selecting a colony of microorganisms on a culture dish; obtaining a sample of said selected colony of microorganisms; depositing at least some of said sample of said selected colony of microorganisms on a target plate; and transferring said target plate with said sample in an apparatus for performing MALDI for identification of said sample of said selected colony of microorganisms. It appears that the problems mentioned above for the greater part find their cause therein that the steps are performed manually and these steps are therefore prone to undesired variance and mistakes, leading to incorrect results from the MALDI-instrument, additional costs and loss of time. By automating each of the steps these problems can be overcome to at least a large extent. In the present field it has been taken for granted that at least some of the steps only could be performed manually, however in contrast hereto the present invention provides the possibility for the first time to automate all the steps necessary for locating and selecting a colony of microorganisms and identifying microorganisms in said selected colony using MALDI.

In an embodiment of a method according to the invention the step of depositing at least some of said sample of said selected colony of microorganisms on a target plate is performed by directly placing said obtained sample of said selected colony of microorganisms on said target plate. By directly placing a sample on a target plate there is no need to first prepare a suspension of said sample, thereby circumventing every problem which might arise from preparing such a suspension. Preferably the method comprises the further automated step of overlaying a drop of a MALDI matrix solution on the portion of the sample deposited on the target plate.

In an alternative embodiment of a method according to the invention the step of depositing at least some of said sample of said selected colony of microorganisms on a target plate is performed by the automated steps of: transferring said obtained sample into a suspension tube containing an amount of a suspension medium; preparing a sample suspension by transferring at least a portion of said obtained sample into said suspension medium; obtaining a drop of said sample suspension; and transferring said drop of sample suspension onto said target plate. By completely automating the preparation of a suspension the invention provides an accurate and reproducible method of using suspensions for identifying microorganisms using MALDI. In particular when the method further comprises the automated step of overlaying a drop of a MALDI matrix solution on said drop of sample suspension deposited on the target plate, the inventive method is extremely suitable for characterization of microorganisms. The best analysis results can be obtained in a further embodiment of a method according to the invention in which said drop of sample suspension deposited on the target plate is allowed to dry before said drop of MALDI matrix solution is overlaid. This alternative method of using a suspension is furthermore extremely useful in case another test or analysis is to be performed on the sample of the colony of microorganisms. Such additional analysis can in a particularly reproducible and efficient manner be realized in an embodiment of a method according to the invention in which the method further comprises the automated steps of: obtaining a second drop of said sample suspension; depositing said second drop of sample suspension on a test culture dish; and transferring said test culture dish to an apparatus for performing a susceptibility test or another additional analysis. Consequently the inventive method can be used to automatically obtain or pick a sample which can be fed into available ID/AST instruments including but not limited to BACTEC™, Phoenix, MGIT, BacT/Alert.

The present invention also provides the possibility of performing such additional analysis in case no suspension is made from an obtained sample. In this situation a particular advantageous embodiment of a method according to the invention further comprises the automated steps of: obtaining a second sample of a colony of microorganisms from the culture dish; transferring said second sample of said selected colony of microorganisms; depositing at least some of said second sample of said selected colony of microorganisms on a test culture dish; and transferring said test culture dish to an apparatus for performing a susceptibility test or another additional test.

Since for performing characterization and identification of microorganisms normally a plurality of colonies is grown on a culture dish, it is furthermore important that a sample is obtained from a colony of interest. If samples are taken from non-interesting colonies the efficient use of time and the MALDI-instrument is compromised. According to the knowledge of the applicant up till now no automated process or apparatus exists for discriminating interesting colonies from non-interesting ones. However, the process of discriminating colonies can be at least partly automated under maintaining a very high certainty of correct discrimination in an embodiment of a method in accordance with the invention in which the method comprises before the automated step of locating and selecting a colony of microorganisms on a culture dish, the step of providing a culture dish comprising a number of colonies of microorganisms, obtaining an initial image of said culture dish including all the colonies of microorganisms, displaying said initial image of said culture dish including all the colonies of microorganisms on a display, and selecting at least one colony of microorganisms in said initial image. In this manner a researcher or analyst can select colonies of interest based on thorough education and knowledge. In a particular embodiment said culture dish is provided with an individual identification identifying said culture dish, such as a bar code, and the method further comprises the step of storing said initial image of said culture dish including all colonies, storing information regarding said at least one selected colony of microorganisms, storing said identification of said culture dish in a memory of a central control computer. In an additional embodiment the researcher or analyst can manually enter processing instructions regarding the processing to which a selected colony of microorganisms of said culture dish is to be subjected, said processing instructions being stored in said memory of said central control computer for later use.

In a further embodiment of the invention the method comprises the automated steps of positioning said culture dish on a stage for a culture dish, obtaining an image of said culture dish positioned in said stage, obtaining the identification of said culture dish, comparing the image obtained by the imaging device of said picking tool device with the stored initial image of said culture dish for obtaining information regarding the location of the selected colony of microorganisms and optionally for obtaining the processing instructions regarding the processes to be performed on said selected colony of microorganisms. By comparing the image of the culture dish when it is placed in the picking tool device with the initial image, the location of the selected colonies can be obtained automatically, for example by computerized image comparison.

In still a further embodiment of a method according to the invention the method comprises the step of automatic preparing a suspension of a sample of microorganisms comprising the steps of:

providing a first picking tool and providing a positioning device with a picking tool holder for holding a picking tool, said positioning device being arranged for positioning a picking tool in a starting position above the obtained location of the selected colony of microorganisms on the culture dish and for automatically lowering and raising a picking tool towards and away from the culture dish and for positioning a picking tool in a transfer position, respectively;

positioning said first picking tool in said picking tool holder of the positioning device;

by said positioning device positioning the first picking tool in the starting position above the obtained location of the selected colony of microorganisms on the culture dish, automatically lowering the first picking tool towards the culture dish into contact with the microorganism to pick up a sample of said microorganism, automatically raising the first picking tool with said sample of the microorganism away from the culture dish to the transfer position;

providing a suspension tube holder for holding a suspension tube;

positioning a suspension tube in the suspension tube holder;

providing an automatic suspension medium dispenser for automatically dispensing a suspension medium in a suspension tube held in the suspension tube holder;

by the automatic dispenser automatically supplying an initial amount of suspension medium into the suspension tube held in the suspension tube holder;

providing a transferring device for automatically transferring a picking tool from the transfer position of the positioning device to a position above a suspension tube held in the suspension tube holder, and for lowering and raising a picking tool into and away from a suspension medium contained in a suspension tube, and for positioning a picking tool in a waiting position above a suspension tube held in the suspension tube holder, respectively;

by said transferring device automatically transferring said first picking tool with the sample of the microorganism from the transfer position of the positioning device to a position above the suspension tube held in the suspension tube holder, lowering said first picking tool with the sample of the microorganism into the suspension medium contained in the suspension tube; by the transferring device oscillating the first picking tool in a linear vertical movement for a period of time while the first picking tool with the sample of said microorganism is submerged in the suspension medium; and after said period of time has elapsed raising the first picking tool away from the suspension medium contained in the suspension tube to the waiting position;

providing a turbidity meter for performing measurements of the turbidity of a suspension medium contained in a suspension tube held in the suspension tube holder;

at least after the period of time during which the picking tool is oscillated has elapsed measuring the turbidity of the suspension medium contained in the suspension tube held in the suspension tube holder by the turbidity meter and providing a final measurement value indicative of the measured turbidity;

providing a controller communicatively connected to the positioning device, the transferring device, the automatic suspension medium dispenser and the turbidity meter for automatically controlling the movement of the positioning device, the movement of the transferring device, the operation of the automatic suspension medium dispenser and the operation of the turbidity meter, respectively;

by said controller:
a) determining whether the final measurement value is above a first threshold value previously stored in a memory of the controller, if yes perform step b); or whether the final measurement value is identical to or below the first threshold value and identical to or above a second threshold value previously stored in the memory of the controller, said first threshold value being equal to or greater than the second threshold value, if yes perform step c); or whether the final measurement value is below the second threshold value, if yes then perform step d);
b) controlling the automatic suspension medium dispenser to supply an additional amount of suspension medium into the suspension tube;
c) providing a signal that the suspension tube with the suspension can be removed from the suspension tube holder for further processing; or
d) providing a further picking tool; positioning said further picking tool in said picking tool holder of the positioning device; by said positioning device positioning the further picking tool in the starting position above the culture dish, automatically lowering the further picking tool towards the culture dish into contact with the microorganism to pick up an additional sample of said microorganism, automatically raising the further picking tool with said sample of the microorganism away from the culture dish to the transfer position; by said transferring device automatically transferring said further picking tool with the additional sample of the microorganism from the transfer position of the positioning device to a position above the suspension tube held in the suspension tube holder, lowering said further picking tool with the additional sample of the microorganism into the suspension medium contained in the suspension tube; by the transferring device oscillating the further picking tool in a linear vertical movement for a period of time while the further picking tool with the additional sample of said microorganism is submerged in the suspension medium; and after said period of time has elapsed raising the further picking tool away from the suspension medium contained in the suspension tube to the waiting position; at least after the period of time during which the further picking tool is oscillated has elapsed measuring the turbidity of the suspension medium contained in the suspension tube held in the suspension tube holder by the turbidity meter and providing an additional final measurement value indicative of the measured turbidity; and performing step a). In this manner it is possible to prepare a suspension of a sample of a microorganism in an advanced automatic manner while by means of the controller and the turbidity meter it is possible to provide a suspension tube containing a suspension medium which contains an amount of microorganism which is always sufficient (and reproducible) to perform a correct analysis of the microorganism.

In an embodiment of a method for automatic preparing a suspension of a sample of microorganisms according to the invention the controller is arranged such that the step of measuring the turbidity of the suspension medium contained in the suspension tube held in the suspension tube holder by the turbidity meter is additionally performed during the period of time during which the picking tool is oscillated, wherein the turbidity meter is arranged for providing an on-line measurement value indicative of the measured turbidity during the period of time during which the picking tool is oscillated to the controller. In this way an extremely fast automatic determination of the amount of microorganism in the suspension can be obtained. In particular, if during oscillation the on-line measurement value of the turbidity is equal to or lower than the first threshold value and equal to or greater than the second threshold value the controller controls the movement of the transferring device such that the picking tool is raised to the waiting position, and the controller further provides a signal that the suspension tube with the suspension can be removed from the suspension tube holder for further processing. In this manner the oscillation of the picking tool is stopped when the suspension medium contains a sufficient amount of microorganisms, so that the method can be performed extremely time efficient.

The mutual arrangement of the pick tool and the sensors of turbidity meter is such that during the oscillation of the pick tool the pick tool does not obstruct the pathway of the turbidity meter.

In a further embodiment of a method for automatic preparing a suspension of a sample of microorganisms according to the invention the controller is arranged such as to control the turbidity meter that the step of measuring the turbidity of the suspension medium contained in the suspension tube held in the suspension tube holder by the turbidity meter is started before the picking tool is submerged in the suspension medium contained in the suspension tube. In this way it is for example possible to check whether the initial suspension medium used is not contaminated. Furthermore, this provides an indication of the starting value for the turbidity which is useful in determining the final measurement value.

In a still further embodiment of a method for automatic preparing a suspension of a sample of microorganisms according to the invention the method further comprises the step of providing as suspension tube holder for holding a suspension tube a rotatable suspension tube holder for rotating a suspension tube held in the rotatable suspension tube holder, the step of arranging the controller such that it is communicatively connected to the rotatable suspension tube holder for controlling the rotation of the suspension tube holder, and the step of arranging the controller such that the suspension tube is rotated during measurement of the turbidity of the suspension medium contained in the suspension tube. Such a rotation of the suspension tube enables that the turbidity measurements can be performed at a number of positions within the suspension tube which are rotationally spaced from each other leading to a more correct final measurement of the turbidity of the suspension. The rotation as such is not necessary for releasing the sample from the picking tool, the oscillational linear vertical movement of the picking tool is more than sufficient to release the sample.

Although a further picking tool can be used that is different from the first picking tool, the method can be performed in an economical way when in step d) the first picking tool is provided as further picking tool; and the positioning of said further picking tool in said picking tool holder of the positioning device is performed by the transferring device under control of the controller.

In a still further embodiment of a method for automatic preparing a suspension of a sample of microorganisms according to the invention the additional amount of suspension medium is determined by the controller based on the initial amount of suspension medium, the final measurement value and the value of the first and/or second threshold value. This makes it possible to use just enough additional suspension medium as necessary and thus in this embodiment as less as possible suspension medium can be used.

Since according to the inventive method for automatic preparing a suspension of a sample of microorganisms the picking tool is oscillated in a vertical linear movement relative to the suspension tube, the dimension of the suspension tube can be relatively small. This makes it possible that in an embodiment of a method according to the invention the controller can be arranged for controlling the automatic suspension medium dispenser such that the supplied initial amount is about 0.5-2 ml, preferably about 1 ml. Such a relatively small amount of suspension medium is sufficient for preparing a correct suspension of a sample of microorganisms. In such a method for automatic preparing a suspension of a sample of microorganisms it is this possible to use as suspension tube a suspension tube having a substantially circular cross-section having a diameter of about 6 to about 12 mm, preferably about 10 mm, which is relatively small when compared to the traditional tubes which have a diameter of about 16 mm. With such a relatively small suspension tube a correct release of the sample from the picking tool is obtained when the controller is arranged for controlling the oscillation of the transferring device such that the picking tool oscillates at a frequency between about 5 Hz to about 120 Hz, preferably about 30 Hz to about 90 Hz, most preferably about 50 Hz. Preferably the controller is arranged for controlling the oscillation of the transferring device such that the picking tool oscillates with an amplitude of about 0.5 mm to about 4 mm, preferably about 2 mm to about 3 mm, which results in an optimal release of the sample from the picking tool. In case the controller is arranged for controlling the oscillation of the transferring device such that the period of time during which the picking tool oscillates is about 3 seconds to about 10 seconds, preferably about 6 seconds, it appears that in practically all cases the complete sample can be released from the picking tool.

The values for the frequency, amplitude and duration are dependent on the properties of the specific microorganism and, for example its adherence to the picking tool. From inspection by imaging it can be deduced whether or not the sample has at least for the greater part been released from the picking tool by first using the above mentioned preferred values. If there is still some material left on the picking tool than the vertical oscillation is repeated within the given ranges at different values.

An automated method for preparing a suspension of a sample of microorganisms according to the invention can be obtained when the method additionally comprises the step of providing an automatic culture dish positioning and removing device for automatically positioning and removing a culture dish comprising said microorganism on and from the stage, respectively. The controller is then arranged such that it is communicatively connected to the automatic culture dish positioning and removing device for controlling the operation of the automatic culture dish positioning and removing device. In this manner positioning a culture dish comprising said microorganism on the stage can be performed automatically under control of the controller. A further automation is realized by providing an automatic suspension tube positioning and removing device for automatically positioning and removing a suspension tube in and from the suspension tube holder, respectively. The controller is then arranged such that it is communicatively connected to the automatic suspension tube positioning and removing device for controlling the operation of the automatic suspension tube positioning and removing device, so that positioning of a suspension tube in the suspension tube holder can be performed automatically under control of the controller. Advantageously the controller is then arranged such that a culture dish is allowed to be automatically removed from the stage by the automatic culture dish positioning and removing device only after the signal that the suspension tube with the suspension can be removed from the suspension tube holder for further processing has been provided. Furthermore it is then preferred that the controller is arranged such that a suspension tube holder is automatically removed from the suspension tube holder by the automatic suspension tube positioning and removing device only after the signal that the suspension tube with the suspension can be removed from the suspension tube holder for further processing has been provided.

In still a further embodiment of a method according to the invention, the method comprises the step of providing an identifying mark on the suspension tube, and the step of storing the identifying mark of said suspension tube together with the properties of the suspension with a link to the identity of the culture dish from which the selected colony of microorganisms was obtained in the memory of said central control computer the method can not only be automatically operated in an extremely efficient manner but also the correct and fast processing of the obtained analysis results is improved.

In a still further embodiment of a method according to the invention, wherein the processing instructions for a selected colony of microorganisms indicate to directly place said obtained sample of said selected colony of microorganisms on said target plate, the method comprises the following automated steps: providing a first picking tool and providing a positioning device with a picking tool holder for holding a picking tool, said positioning device being arranged for positioning a picking tool in a starting position above the obtained location of the selected colony of microorganisms on the culture dish and for automatically lowering and raising a picking tool towards and away from the culture dish and for positioning a picking tool in a transfer position, respectively; positioning said first picking tool in said picking tool holder of the positioning device; by said positioning device positioning the first picking tool in the starting position above the obtained location of the selected colony of microorganisms on the culture dish, automatically lowering the first picking tool towards the culture dish into contact with the microorganism to pick up a sample of said microorganism, automatically raising the first picking tool with said sample of the microorganism away from the culture dish to the transfer position; providing a target plate holder for holding a target plate, said target plate having a plurality of depositing spots; positioning a target plate in the target plate holder; providing a transferring device for automatically transferring the picking tool from the transfer position of the positioning device to a position above one of the depositing spots of the target plate, and for lowering the picking tool such that the sample of the colony of microorganisms present on the picking tool comes into contact with the target plate, moving the picking tool in a plane parallel to the plane of the target plate such that the sample of the colony of microorganisms is deposited on the depositing spot, in particular covering at most approximately half of said one of the depositing spots of the target plate; and raising said picking tool from the target plate. By performing the deposition of the sample automatically a more reproducible and accurate deposition of the sample on the depositing spot can be obtained then by manually depositing a sample. Furthermore it appears then when the sample covers at most approximately half of said one of the depositing spots of the target plate, the analysis results obtained from the MALDI-instrument of the part of the depositing spot which initially was not covered with the sample are surprisingly extremely more accurate than the analysis results obtained from the MALDI-instrument of the part of the depositing spot which initially was covered with the sample. While the inventors do not wish to be bound by a particular theory, it is thought that the crystallization which takes place after a drop of matrix material has been overlaid on the sample covering part of the depositing spot ensures that also the part of the depositing spot which was not covered contains an amount of sample material, and that this amount is extremely suitable for providing excellent analysis results.

In an alternative embodiment of a method according to the invention, wherein in case the processing instructions for a selected colony of microorganisms indicate to obtain a drop from said sample suspension and to transfer said drop onto said target plate, the method comprises the following automated steps: providing a pipetting tool in said picking tool device and providing a positioning device with a pipetting tool holder for holding said pipetting tool, said positioning device being arranged for positioning said pipetting tool in a starting position above the suspension tube and for automatically lowering and raising the pipetting tool into and out of the suspension and for positioning the pipetting tool in a transfer position, respectively; positioning said pipetting tool in said pipetting tool holder of the positioning device; by said positioning device positioning the pipetting tool in the starting position above the suspension tube, lowering the pipetting tool into the suspension in said suspension tube, operating the pipetting tool to pick up an amount of suspension, raising the pipetting tool with said amount of suspension to the transfer position; said pipetting tool comprising a pressurizable chamber closed by a controlled valve for containing the amount of suspension medium; providing a target plate holder for holding a target plate, said target plate having a plurality of depositing spots; positioning a target plate in the target plate holder; providing a transferring device for automatically transferring the pipetting tool from the transfer position of the positioning device to a position above one of the depositing spots of the target plate, and for lowering the pipetting tool to a predefined distance above the target plate, pressurizing the chamber to a pressure in a range of about 0.5 bar to 1.1 bar, and opening the valve for such a time that a drop of suspension with a volume in a range of about 0.5 to 3.0 µl is deposited on the depositing spot, in particular covering at most approximately half of said one of the depositing spots of the target plate; and raising said pipetting tool from the target plate. In dependence of the properties of the specific microorganism, e.g. its stickiness, the pressure value and the opening time can be adjusted to obtain a small drop of suspension which can be reproducibly prepared and which as a result of the automated process can be deposited accurately on the target plate.

In order to avoid cross-contamination in a preferred embodiment of a method according to the invention the shape of the pipetting tool, in particular the dispensing tip thereof, is such that depositing the drop of suspension on the target plate takes place in a splash free manner. It has appeared that depending on the kind of microorganism used, and especially the stickiness thereof, in addition to choosing a correct pressure in the range mentioned above and opening time of the valve in the range mentioned above a suitable shape of the pipetting tool ensures that a drop of suspension can be is deposited in a splash free manner.

In a further embodiment of a method according to the invention in which the method comprises the step of providing an identifying mark on the target plate and optionally providing an identifying mark on the depositing spots of said target plate, and the step of storing the identifying mark of said target plate and depositing spots together with the properties of the suspension with a link to the identity of the culture dish from which the selected colony of microorganisms was obtained in the memory of said central control computer the method can not only be automatically operated in an extremely efficient manner but also the correct and fast processing of the obtained analysis results is improved.

The present invention further relates to a method for automatic preparing a suspension of a sample of microorganisms, said method comprises the steps of:

providing a stage for a culture dish comprising said microorganism;

positioning a culture dish comprising said microorganism on the stage;

providing a first picking tool and providing a positioning device with a picking tool holder for holding a picking tool, said positioning device being arranged for positioning a picking tool in a starting position above the culture dish and for automatically lowering and raising a picking tool towards and away from the culture dish and for positioning a picking tool in a transfer position, respectively;

positioning said first picking tool in said picking tool holder of the positioning device;

by said positioning device positioning the first picking tool in the starting position above the culture dish, automatically lowering the first picking tool towards the culture dish into contact with the microorganism to pick up a sample of said microorganism, automatically raising the first picking tool with said sample of the microorganism away from the culture dish to the transfer position;

providing a suspension tube holder for holding a suspension tube;

positioning a suspension tube in the suspension tube holder;

providing an automatic suspension medium dispenser for automatically dispensing a suspension medium in a suspension tube held in the suspension tube holder;

by the automatic dispenser automatically supplying an initial amount of suspension medium into the suspension tube held in the suspension tube holder;

providing a transferring device for automatically transferring a picking tool from the transfer position of the positioning device to a position above a suspension tube held in the suspension tube holder, and for lowering and raising a picking tool into and away from a suspension medium contained in a suspension tube, and for positioning a picking tool in a waiting position above a suspension tube held in the suspension tube holder, respectively;

by said transferring device automatically transferring said first picking tool with the sample of the microorganism from the transfer position of the positioning device to a position above the suspension tube held in the suspension tube holder, lowering said first picking tool with the sample of the microorganism into the suspension medium contained in the suspension tube; by the transferring device oscillating the first picking tool in a linear vertical movement for a period of time while the first picking tool with the sample of said microorganism is submerged in the suspension medium; and after said period of time has elapsed raising the first picking tool away from the suspension medium contained in the suspension tube to the waiting position;

providing a turbidity meter for performing measurements of the turbidity of a suspension medium contained in a suspension tube held in the suspension tube holder;

at least after the period of time during which the picking tool is oscillated has elapsed measuring the turbidity of the suspension medium contained in the suspension tube held in the suspension tube holder by the turbidity meter and providing a final measurement value indicative of the measured turbidity;

providing a controller communicatively connected to the positioning device, the transferring device, the automatic suspension medium dispenser and the turbidity meter for automatically controlling the movement of the positioning device, the movement of the transferring device, the operation of the automatic suspension medium dispenser and the operation of the turbidity meter, respectively;

by said controller:
a) determining whether the final measurement value is above a first threshold value previously stored in a memory of the controller, if yes perform step b); or whether the final measurement value is identical to or below the first threshold value and identical to or above a second threshold value previously stored in the memory of the controller, said first threshold value being equal to or greater than the second threshold value, if yes perform step c); or whether the final measurement value is below the second threshold value, if yes then perform step d);
b) controlling the automatic suspension medium dispenser to supply an additional amount of suspension medium into the suspension tube;
c) providing a signal that the suspension tube with the suspension can be removed from the suspension tube holder for further processing; or
d) providing a further picking tool; positioning said further picking tool in said picking tool holder of the positioning device; by said positioning device positioning the further picking tool in the starting position above the culture dish, automatically lowering the further picking tool towards the culture dish into contact with the microorganism to pick up an additional sample of said microorganism, automatically raising the further picking tool with said sample of the microorganism away from the culture dish to the transfer position; by said transferring device automatically transferring said further picking tool with the additional sample of the microorganism from the transfer position of the positioning device to a position above the suspension tube held in the suspension tube holder, lowering said further picking tool with the additional sample of the microorganism into the suspension medium contained in the suspension tube; by the transferring device oscillating the further picking tool in a linear vertical movement for a period of time while the further picking tool with the additional sample of said microorganism is submerged in the suspension medium; and after said period of time has elapsed raising the further picking tool away from the suspension medium contained in the suspension tube to the waiting position; at least after the period of time during which the further picking tool is oscillated has elapsed measuring the turbidity of the suspension medium contained in the suspension tube held in the suspension tube holder by the turbidity meter and providing an additional final measurement value indicative of the measured turbidity; and performing step a). In this manner it is possible to prepare a suspension of a sample of a microorganism in an advanced automatic manner while by means of the controller and the turbidity meter it is possible to provide a suspension tube containing a suspension medium which contains an amount of microorganism which is always sufficient (and reproducible) to perform a correct analysis of the microorganism.

In an embodiment of a method for automatic preparing a suspension of a sample of microorganisms according to the invention the controller is arranged such that the step of measuring the turbidity of the suspension medium contained in the suspension tube held in the suspension tube holder by the turbidity meter is additionally performed during the period of time during which the picking tool is oscillated, wherein the turbidity meter is arranged for providing an on-line measurement value indicative of the measured turbidity during the period of time during which the picking tool is oscillated to the controller. In this way an extremely fast automatic determination of the amount of microorganism in the suspension can be obtained. In particular, if during oscillation the on-line measurement value of the turbidity is equal to or lower than the first threshold value and equal to or greater than the second threshold value the controller controls the movement of the transferring device such that the picking tool is raised to the waiting position, and the controller further provides a signal that the suspension tube with the suspension can be removed from the suspension tube holder for further processing.

In a further embodiment of a method for automatic preparing a suspension of a sample of microorganisms according to the invention the controller is arranged such as to control the turbidity meter that the step of measuring the turbidity of the suspension medium contained in the suspension tube held in the suspension tube holder by the turbidity meter is started before the picking tool is submerged in the suspension medium contained in the suspension tube. In this way it is for example possible to check whether the initial suspension medium used is not contaminated. This can for example be done by performing a turbidity measurement of a suspension tube and compare the obtained value with a predetermined value indicating that the suspension is uncontaminated. In case the difference exceeds a threshold value, then e.g. a warning signal can be given indicating that the suspension is contaminated.

In a still further embodiment of a method for automatic preparing a suspension of a sample of microorganisms according to the invention the method further comprises the step of providing as suspension tube holder for holding a suspension tube a rotatable suspension tube holder for rotating a suspension tube held in the rotatable suspension tube holder, the step of arranging the controller such that it is communicatively connected to the rotatable suspension tube holder for controlling the rotation of the suspension tube holder, and the step of arranging the controller such that the suspension tube is rotated during measurement of the turbidity of the suspension medium contained in the suspension tube. Such a rotation of the suspension tube enables that the turbidity measurements can be performed at a number of positions within the suspension tube which are rotationally spaced from each other leading to a more correct final measurement of the turbidity of the suspension. The rotation as such is not necessary for releasing the sample from the picking tool, the oscillational linear vertical movement of the picking tool is more than sufficient to release the sample.

Although a further picking tool can be used that is different from the first picking tool, the method can be performed in an economical way when in step d) the first picking tool is provided as further picking tool; and the positioning of said further picking tool in said picking tool holder of the positioning device is performed by the transferring device under control of the controller.

In a still further embodiment of a method for automatic preparing a suspension of a sample of microorganisms according to the invention the additional amount of suspension medium is determined by the controller based on the initial amount of suspension medium, the final measurement value and the value of the first and/or second threshold value. This makes it possible to use just enough additional suspension medium as necessary and thus in this embodiment as less as possible suspension medium can be used. In case the measured value indicates that the amount of microorganisms is too low, then the control system controls the picking tool to obtain an additional sample from the same selected colony, and the process is repeated.

Since according to the inventive method for automatic preparing a suspension of a sample of microorganisms the picking tool is oscillated in a vertical linear movement only, the dimension of the suspension tube can be relatively small. This makes it possible that in an embodiment of a method according to the invention the controller can be arranged for controlling the automatic suspension medium dispenser such that the supplied initial amount is about 0.5-2 ml, preferably about 1 ml. Such a relatively small amount of suspension medium is sufficient for preparing a correct suspension of a sample of microorganisms. In such a method for automatic preparing a suspension of a sample of microorganisms it is this possible to use as suspension tube a suspension tube having a substantially circular cross-section having a diameter of about 6 to about 12 mm, preferably about 10 mm, which is relatively small when compared to the traditional tubes which have a diameter of about 16 mm. With such a relatively small suspension tubes a correct release of the sample from the picking tool is obtained when the controller is arranged for controlling the oscillation of the transferring device such that the picking tool oscillates at a frequency between about 5 Hz to about 120 Hz, preferably about 30 Hz to about 90 Hz, most preferably about 50 Hz. Preferably the controller is arranged for controlling the oscillation of the transferring device such that the picking tool oscillates with an amplitude of about 0.5 mm to about 4 mm, preferably about 2 mm to about 3 mm, which results in an optimal release of the sample from the picking tool. In case the controller is arranged for controlling the oscillation of the transferring device such that the period of time during which the picking tool oscillates is about 3 seconds to about 10 seconds, preferably about 6 seconds, it appears that in practically all cases the complete sample can be released from the picking tool.

The invention further relates to an apparatus for automatic preparation of a suspension of a sample of microorganisms for performing a method for locating and selecting a colony of microorganisms on a culture dish and identifying microorganisms in said selected colony using MALDI or for performing a step of a method for automatic preparing a suspension of a sample of microorganisms according to the inventive methods, said apparatus comprising:

a stage for a culture dish comprising said microorganism;

a first and a further picking tool and a positioning device with a picking tool holder for holding a picking tool, said positioning device being arranged for positioning a picking tool in a starting position above the culture dish and for automatically lowering and raising a picking tool towards and away from the culture dish and for positioning a picking tool in a transfer position, respectively;

a suspension tube holder for holding a suspension tube;

an automatic suspension medium dispenser for automatically dispensing a suspension medium in a suspension tube held in the suspension tube holder;

a transferring device for automatically transferring a picking tool from the transfer position of the positioning device to a position above a suspension tube held in the suspension tube holder, and for lowering and raising a picking tool into and away from a suspension medium contained in a suspension tube, and for positioning a picking tool in a waiting position above a suspension tube held in the suspension tube holder, respectively, said transferring device further being arranged for oscillating a picking tool in a linear vertical movement for a period of time;

a turbidity meter for performing measurements of the turbidity of a suspension medium contained in a suspension tube held in the suspension tube holder and for providing a final measurement value indicative of the measured turbidity;

a controller communicatively connected to the positioning device, the transferring device, the automatic suspension medium dispenser and the turbidity meter for automatically controlling the movement of the positioning device, the movement of the transferring device, the operation of the automatic suspension medium dispenser and the operation of the turbidity meter, respectively;

said controller being arranged for:
a) determining whether the final measurement value is above a first threshold value previously stored in a memory of the controller, if yes said controller being arranged for performing step b); or whether the final measurement value is identical to or below the first threshold value and identical to or above a second threshold value previously stored in the memory of the controller, said first threshold value being equal to or greater than the second threshold value, if yes said controller being arranged for performing step c); or whether the final measurement value is below the second threshold value, if yes said controller being arranged for performing step d);
b) controlling the automatic suspension medium dispenser to supply an additional amount of suspension medium into the suspension tube;
c) providing a signal that the suspension tube with the suspension can be removed from the suspension tube holder for further processing; or
d) positioning said further picking tool in said picking tool holder of the positioning device; by said positioning device positioning the further picking tool in the starting position above the culture dish, automatically lowering the further picking tool towards the culture dish into contact with the microorganism to pick up an additional sample of said microorganism, automatically raising the further picking tool with said sample of the microorganism away from the culture dish to the transfer position; by said transferring device automatically transferring said further picking tool with the additional sample of the microorganism from the transfer position of the positioning device to a position above the suspension tube held in the suspension tube holder, lowering said further picking tool with the additional sample of the microorganism into the suspension medium contained in the suspension tube; by the transferring device oscillating the further picking tool in a linear vertical movement for a period of time while the further picking tool with the additional sample of said microorganism is submerged in the suspension medium; and after said period of time has elapsed raising the further picking tool away from the suspension medium contained in the suspension tube to the waiting position; at least after the period of time during which the further picking tool is oscillated has elapsed measuring the turbidity of the suspension medium contained in the suspension tube held in the suspension tube holder by the turbidity meter and providing an additional final measurement value indicative of the measured turbidity; and performing step a).

In a further embodiment of an apparatus according to the invention the controller is arranged for controlling the turbidity meter such that measuring the turbidity of the suspension medium contained in the suspension tube held in the suspension tube holder by the turbidity meter is started before the picking tool is submerged in the suspension medium contained in the suspension tube.

In a still further embodiment of an apparatus according to the invention the suspension tube holder for holding a suspension tube is a rotatable suspension tube holder for rotating a suspension tube held in the rotatable suspension tube holder, wherein the controller is arranged for being communicatively connected to the rotatable suspension tube holder for controlling the rotation of the suspension tube holder, and said controller is arranged for rotating the suspension tube during measurement of the turbidity of the suspension medium contained in the suspension tube.

In an advantageous embodiment of an apparatus according to the invention in step d) the first picking tool is provided as further picking tool; and said controller is arranged for controlling the transferring device for positioning said further picking tool in said picking tool holder of the positioning device.

Preferably the controller is arranged for determining the additional amount of suspension medium based on the initial amount of suspension medium, the final measurement value and the value of the first and/or second threshold value. In particular the controller is arranged for controlling the automatic suspension medium dispenser such that the supplied initial amount is about 0.5-2 ml, preferably about 1 ml. In a further embodiment of an apparatus according to the invention the controller is arranged for controlling the oscillation of the transferring device such that the picking tool oscillates at a frequency between about 5 Hz to about 120 Hz, preferably about 30 Hz to about 90 Hz, most preferably about 50 Hz. Furthermore the controller can be arranged for controlling the oscillation of the transferring device such that the picking tool oscillates with an amplitude of about 0.5 mm to about 4 mm, preferably about 2 mm to about 3 mm, and for controlling the oscillation of the transferring device such that the period of time during which the picking tool oscillates is about 3 seconds to about 10 seconds, preferably about 6 seconds.

In an inventive device for the automatic preparation of a suspension of a sample of microorganisms the suspension tube can have a substantially circular cross-section with a diameter of about 6 to about 12 mm, preferably about 10 mm.

A fully automatic device according to the invention when the apparatus comprises an automatic culture dish positioning and removing device for automatically positioning and removing a culture dish comprising said microorganism on and from the stage, respectively, said controller being arranged for being communicatively connected to the automatic culture dish positioning and removing device for controlling the operation of the automatic culture dish positioning and removing device, and for automatically positioning a culture dish comprising said microorganism on the stage, and when the apparatus comprises an automatic suspension tube positioning and removing device for automatically positioning and removing a suspension tube in and from the suspension tube holder, respectively, said controller being arranged for being communicatively connected to the automatic suspension tube positioning and removing device for controlling the operation of the automatic suspension tube positioning and removing device, and for automatically positioning a suspension tube in the suspension tube holder. In this case it is then preferred that the controller is arranged for allowing a culture dish to be automatically removed from the stage by the automatic culture dish positioning and removing device only after the signal that the suspension tube with the suspension can be removed from the suspension tube holder for further processing has been provided. In addition the controller is then preferably arranged for automatically removing a suspension tube holder from the suspension tube holder by the automatic suspension tube positioning and removing device only after the signal that the suspension tube with the suspension can be removed from the suspension tube holder for further processing has been provided.

The invention still further relates to a method for automatically depositing a sample of a colony of microorganisms on a depositing spot of a target plate for MALDI, wherein the method comprises the step of depositing the sample of the colony of microorganisms on the depositing spot such that the sample covers at most approximately half of said one of the depositing spots of the target plate. It has been discovered that then when the sample covers at most approximately half of said one of the depositing spots of the target plate, the analysis results obtained from the MALDI-instrument of the part of the depositing spot which initially was not covered with the sample are surprisingly extremely more accurate than the analysis results obtained from the MALDI-instrument of the part of the depositing spot which initially was covered with the sample. It is assumed that the crystallization which takes place after a drop of matrix material has been overlaid on the sample covering part of the depositing spot ensures that also the part of the depositing spot which was not covered contains an amount of sample material, and that this amount is extremely suitable for providing excellent analysis results. The physical or chemical processes which are the cause for this effect are, at the moment, unclear, but perhaps more clarity might arise when the fundamental processes underlying MALDI are known. In an embodiment of such a method the sample of a colony of microorganisms is in the form of a suspension, wherein the sample of the suspension is deposited on a depositing spot of the target plate in the form of a drop having a volume in a range of about 0.5 to 3.0 µl.

The invention still further relates to a method for automatically depositing a drop of a suspension containing a sample of a colony of microorganisms on a depositing spot of a target plate for MALDI, wherein the method comprises the following automated steps:

providing a pipetting tool in a picking tool device and providing a positioning device with a pipetting tool holder for holding said pipetting tool, said positioning device being arranged for positioning said pipetting tool in a starting position above a suspension tube holding said suspension containing a sample of a colony of microorganisms, and for automatically lowering and raising the pipetting tool into and out of the suspension and for positioning the pipetting tool in a transfer position, respectively;

positioning said pipetting tool in said pipetting tool holder of the positioning device;

by said positioning device positioning the pipetting tool in the starting position above the suspension tube, lowering the pipetting tool into the suspension in said suspension tube, operating the pipetting tool to pick up an amount of suspension, raising the pipetting tool with said amount of suspension to the transfer position; said pipetting tool comprising a pressurizable chamber closed by a controlled valve for containing the amount of suspension medium;

providing a target plate holder for holding the target plate, said target plate having a plurality of depositing spots;

positioning the target plate in the target plate holder;

providing a transferring device for automatically transferring the pipetting tool from the transfer position of the positioning device to a position above one of the depositing spots of the target plate, and for lowering the picking tool to a predefined distance above the target plate, pressurizing the chamber to a pressure in a range of about 0.5 bar to 1.1 bar, and opening the valve for such a time that a drop of suspension with a volume in a range of about 0.5 to 3.0 µl is deposited on said one of the depositing spots; and raising said pipetting tool from the target plate. Preferably the shape of the pipetting tool is such that depositing the drop of suspension on the target plate takes place in a splash free manner. In particular the method comprises pressurizing the chamber to such a pressure in a range of about 0.5 bar to 1.1 bar, and opening the valve for such a time that a drop of suspension with a volume in a range of about 0.5 to 3.0 µl is deposited on at most half said one of the depositing spots. It has been discovered that then when the sample covers at most approximately half of said one of the depositing spots of the target plate, the analysis results obtained from the MALDI-instrument of the part of the depositing spot which initially was not covered with the sample are surprisingly extremely more accurate than the analysis results obtained from the MALDI-instrument of the part of the depositing spot which initially was covered with the sample. It is assumed that the crystallization which takes place after a drop of matrix material has been overlaid on the sample covering part of the depositing spot ensures that also the part of the depositing spot which was not covered contains an amount of sample material, and that this amount is extremely suitable for providing excellent analysis results. The physical or chemical processes which are the cause for this effect are, at the moment, unclear, but perhaps more clarity might arise when the fundamental processes underlying MALDI are known.

BRIEF DESCRIPTION OF THE DRAWINGS

The invention will be further explained with reference to FIG. 1, in which a non-limiting exemplary embodiment of an apparatus of the invention is shown, which FIG. 1 will also be used to explain exemplary embodiments of the method according to the invention.

DETAILED DESCRIPTION

In the present invention MALDI or MALDI-TOF-MS is used to identify microorganisms. In a MALDI TOF MS operation a sample of a colony of microorganisms is spotted or deposited on a target plate which is held in a fixed position in the MALDI-instrument. Such a target plate has a plurality of depositing spots (e.g. from 24 to 384 depositing spots on a single target plate) and these depositing spots have a fixed orientation with regard to the edges of the target plate. The target plate is positioned on an X-Y stage so that an obtained sample of a colony of microorganisms can be deposited on a selected depositing spot, wherein the location where a specific sample has been deposited is indicated by the X-Y parameters and is stored in a memory of a central control computer.

Although not depicted in detail in FIG. 1, the target plate is positioned below a transfer track 18 at a position indicated by B. A sample can be transferred along the transfer track 18 from a culture dish 3 and/or a suspension tube 11 to above the target plate at position B, where the sample is lowered to be deposited on a depositing spot of the target plate.

Although the invention will be described detailed below with reference to preparing a suspension containing a sample and depositing a drop of said suspension on a depositing spot of a target plate, the present invention also relates to directly depositing a sample obtained (picked) from a culture dish onto a depositing spot of a target plate.

In general, in the latter method a colony of microorganisms is automatically located and detected on a culture dish. A sample of said selected colony of microorganisms is obtained in an automated way, e.g. by a picking tool which is brought into contact with the colony. At least some of said sample of said selected colony of microorganisms is directly deposited on a target plate in an automated way, by lowering the picking tool such that the sample of the colony of microorganisms present on the picking tool comes into contact with the target plate, and moving the picking tool in a plane parallel to the plane of the target plate such that the sample of the colony of microorganisms is deposited on the depositing spot, in particular covering at most approximately half of said one of the depositing spots of the target plate. Thereafter the target plate with said sample is automatically transferred into an apparatus for performing MALDI for identification of said sample of said selected colony of microorganisms.

More detailed this method comprises the following automated steps:

providing a first picking tool and providing a positioning device with a picking tool holder for holding a picking tool, said positioning device being arranged for positioning a picking tool in a starting position above the obtained location of the selected colony of microorganisms on the culture dish and for automatically lowering and raising a picking tool towards and away from the culture dish and for positioning a picking tool in a transfer position, respectively;

positioning said first picking tool in said picking tool holder of the positioning device;

by said positioning device positioning the first picking tool in the starting position above the obtained location of the selected colony of microorganisms on the culture dish, automatically lowering the first picking tool towards the culture dish into contact with the microorganism to pick up a sample of said microorganism, automatically raising the first picking tool with said sample of the microorganism away from the culture dish to the transfer position;

providing a target plate holder for holding a target plate, said target plate having a plurality of depositing spots;

positioning a target plate in the target plate holder;

providing a transferring device for automatically transferring the picking tool from the transfer position of the positioning device to a position above one of the depositing spots of the target plate, and for lowering the picking tool such that the sample of the colony of microorganisms present on the picking tool comes into contact with the target plate, moving the picking tool in a plane parallel to the plane of the target plate such that the sample of the colony of microorganisms is deposited on the depositing spot, in particular covering at most approximately half of said one of the depositing spots of the target plate; and raising said picking tool from the target plate. A drop of a MALDI matrix solution is then automatically laid over on the amount of the sample deposited on the target plate.

In case the same colony of microorganisms is to be subjected to another analysis or test, such as but not limited to an Antibiotic Susceptibility Test (AST) a second sample of said selected colony of microorganisms can be obtained in a manner similar to obtaining the initial sample. Since the location of the colony of microorganisms on the culture dish has already been selected, and is therefore "known" to the central control computer, it is possible to easily and reproducibly obtain a second sample from the same colony. At least some of the second sample of said selected colony of microorganisms is then transferred and deposited on a test culture dish, which can for example be automatically positioned at another position below the transfer track 18. Thereafter said test culture dish is automatically transferred to an apparatus for performing a susceptibility test or another additional analysis.

Since for performing characterization and identification of microorganisms normally a plurality of colonies is grown on a culture dish, and in addition a plurality of different culture dishes is used, the invention provides the possibility to identify each culture dish separately, e.g. by means of a bar code, and furthermore each colony of interest on a single culture dish is selected and given an identification mark. Hereto before the automated step of locating and selecting a colony of microorganisms on a culture dish, the method according to the invention comprises a step of providing a culture dish comprising a number of colonies of microorganisms, obtaining an initial image of said culture dish including all the colonies of microorganisms, displaying said initial image of said culture dish including all the colonies of microorganisms on a display, and selecting at least one colony of microorganisms in said initial image. In this manner a researcher or analyst can select colonies of interest based on thorough education and knowledge. Since each culture dish is provided with an individual identification identifying said culture dish, such as a bar code, the initial image of said culture dish including all colonies is stored, and information regarding said at least one selected colony of microorganisms is stored (preferably with links given in the (electronic) initial image), storing all said information and identifications of the culture dish in a memory of a central control computer allows a very correct further processing. In this manner the only manual operation is the act of selecting the interesting colonies, whereas all relevant data are processed in an automated way. Optionally the researcher or analyst can manually enter processing instructions regarding the processing to which a selected colony of microorganisms of said culture dish is to be subjected, said processing instructions being also stored in said memory of said central control computer for later use. After this manual act all the further steps are performed completely automated in a reliable and efficient manner. For this automated further processing the culture dish is automatically positioned on a stage for a culture dish of a picking tool device comprising an imaging device. An image of said culture dish positioned in said picking tool device is obtained, and together with the identification of said culture dish it is possible to compare this image obtained by the imaging device of said picking tool device with the stored initial image of said culture dish and thus derive information regarding the location of the selected colony of microorganisms and optionally regarding the processing instructions regarding the processes to be performed on said selected colony of microorganisms. By comparing the image of the culture dish when it is placed in the picking tool device with the initial image, the location of the selected colonies can be obtained automatically, for example by computerized image comparison. Furthermore each target plate is provided with an identifying mark and optionally each depositing spot of said target plate has an individual identification mark or location identifier, so that after storing the identifying mark of said target plate and depositing spots together with the properties of the suspension with a link to the identity of the culture dish from which the selected colony of microorganisms was obtained in the memory of said central control computer a correct linking of the obtained MALDI results to the specific colony of microorganism under test is possible in a correct and automated way.

Now an embodiment of a method of the invention will be described in which a suspension is made from a sample of a colony of microorganisms picked from a culture dish together with an embodiment of an apparatus for performing such a method.

Figure 1:
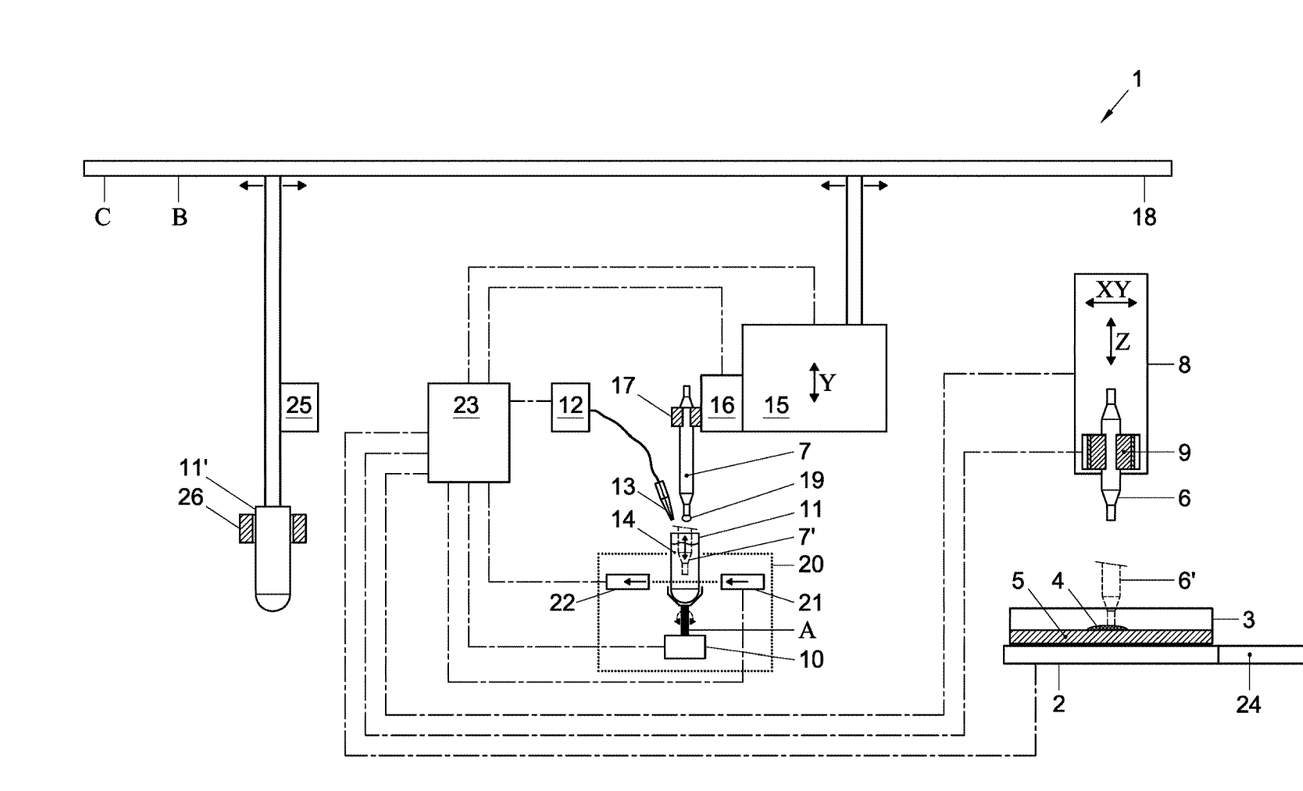

FIG. 1 schematically shows an embodiment of an apparatus 1 for the automatic preparation of a suspension of a sample of a microorganism according to the invention. Said apparatus 1 comprises a stage 2 for a culture dish 3 comprising a microorganism 4 on a nutritional layer 5, such as a layer of agar gel.

The apparatus 1 further comprises a first picking tool 6 and a further picking tool 7. A positioning device 8 comprises a picking tool holder 9 for, in the shown embodiment releasably holding a picking tool, in the embodiment shown in FIG. 1 the picking tool holder 9 holds the first picking tool 6. The positioning device 8 is arranged for positioning the first picking tool 6 in a starting position (shown in solid lines in FIG. 1) above the culture dish 3 and is arranged for automatically lowering and raising the first picking tool 6 towards and away from the culture dish 3, such that the first picking tool 6 can be positioned in a position (indicated with broken lines 6') in which it contacts the microorganism 4 and picks up a sample of said microorganism. After the first picking tool 6 has picked up a sample the positioning device 8 raises and positions the first picking tool 6 in a transfer position, which in the embodiment shown in FIG. 1 is identical to the starting position. In other embodiments the starting and transfer positions may be different from each other.

The apparatus 1 according to the invention further comprises a suspension tube holder 10 for holding a suspension tube 11 which can contain a suspension medium which is dispensed from an automatic suspension medium dispenser 12, which in the shown embodiment has a dispensing nozzle 13 for automatically dispensing a suspension medium 14 in the suspension tube 11 held in the suspension tube holder 10. In the present embodiment the suspension tube holder 10 is a rotatable suspension tube holder for rotating the suspension tube 11 around a vertical axis A.

A transferring device 15 is incorporated in the inventive apparatus 1 for automatically transferring a picking tool from the transfer position of the positioning device 8 to a position above the suspension tube 11 held in the suspension tube holder 10. In the embodiment shown the transferring device 15 comprises a transfer holder 16 with a grasping means 17 for releasably holding a picking tool. The transferring device 15 may in a manner known per se be mounted on a transfer track 18, such as a rail, for linear movement thereon as indicated by the arrows. In this manner the transferring device 15 may be moved to the positioning device 8, such that the grasping means 17 can take over the picking tool from the positioning device 8, the picking tool holder 9 thereof releasing the picking tool after the grasping means 17 has grasped the picking tool. In the embodiment shown in FIG. 1 the second or further picking tool 7 having previously picked up a sample 19 of the microorganism 4 is positioned above the suspension tube 11 by the transferring device 15 in a starting position indicated by solid lines. The transferring device 15 is arranged for lowering the second picking tool 7 into the suspension medium 14 contained in the suspension tube 11, in which position the second picking tool 7' with the sample 19 is submerged in the suspension medium 14 as indicated by broken lines in FIG. 1. In this position the transferring device 15 is activated for oscillating the second picking tool 7 in a linear vertical movement for a period of time which is sufficient for the sample 19 to be released from the second picking tool 7. Thereafter the transferring device 15 positions the second picking tool 7 in a waiting position above the suspension tube 11, which waiting position is in the embodiment shown in FIG. 1 identical to the starting position. In other embodiments the waiting position and the starting position may be different from each other.

The inventive apparatus 1 further is provided with a turbidity meter 20 for performing measurements of the turbidity of the suspension medium 14 contained in the suspension tube 11 held in the suspension tube holder 10. As generally known in the art a turbidity meter can provide measurement values which are a measure of the concentration of material, in the present case the concentration of a microorganism suspended in the suspension medium. In the embodiment shown in FIG. 1 the turbidity meter 20 comprises a laser 21 which transmits laser light towards and through the suspension medium and a sensor 22 which detects the amount of laser light transmitted through the suspension medium. In addition there is a further sensor (not indicated in the drawing) which is e.g. arranged perpendicular to the path of the laser light to detect the amount of laser light which has been scattered by the suspension.

The operation of the inventive device is controlled by a controller 23, for example comprising a microprocessor, which is communicatively connected (as indicated by the signal lines) to the positioning device 8, the transferring device 15, the automatic suspension medium dispenser 12, and the turbidity meter 20 for automatically controlling the movement of the positioning device 8, the movement of the transferring device 15, the operation of the automatic suspension medium dispenser 12 and the operation of the turbidity meter 20, respectively. In addition the controller 23 might be directly communicatively connected to other parts of the apparatus such as for example the picking tool holder 9, the transfer holder 16, the laser 21 and the sensor 22.

In the embodiment shown in FIG. 1 the controller 23 is arranged for controlling the turbidity meter 20 such that the turbidity measurement of the suspension medium 14 is started before the second picking tool 7 is submerged in the suspension medium 14. In addition the controller 23 controls the rotatable suspension tube holder 10 for starting the rotation of the suspension tube 11 held in the holder 10 before the second picking tool 7 is submerged in the suspension medium 14, and for maintaining the rotation of the suspension tube 11 during the measurement of the turbidity of the suspension medium 14. In the shown embodiment the controller 23 controls the turbidity meter 20 such that the measurement of the turbidity is performed during the total period of time during which the second picking tool 7 is oscillated. In this manner the turbidity meter 20 provides an on-line measurement value to the controller 23 which value is indicative of the measured turbidity, and thus the concentration of the microorganism, during the period of time during which the second picking tool is oscillated.

The controller 23 comprises a memory in which a first and a second threshold value are stored, in which said first threshold value is equal to or greater than the second threshold value. If the turbidity measurement value provided by the turbidity meter is equal to or between the first and second threshold value, the concentration/amount of microorganism in the suspension medium is sufficient to allow the suspension tube with the suspension to be further processed. In that case the controller 23 provides a signal that the suspension tube can be processed further. In addition in this situation the second picking tool 7 can be discarded e.g. by transferring the transferring device to a position C in which the grasping means 17 are activated to release the second picking tool 7.

In case the final measurement value of the turbidity meter is above the first threshold value previously stored in a memory of the controller 23 then the concentration of the microorganism is too high to allow the suspension tube to be processed further. In that situation the controller 23 controls the automatic suspension medium dispenser 12 to supply an additional amount of suspension medium into the suspension tube 11. This additional amount of suspension medium is based on the initial amount of suspension medium, the final measurement value and the value of the first and/or second threshold value such that the addition of the additional amount of suspension medium to the suspension medium already present in the suspension tube 11 will lead to a concentration of microorganism in the suspension medium which satisfies the requirement for further processing, as can be confirmed by an additional or further measurement of the turbidity by the turbidity meter 20.

In case the final measurement value of the turbidity meter 20 is below the second threshold value, meaning that the concentration of microorganism in the suspension medium is too low, the controller 23 controls the apparatus 1 such that an additional sample of microorganism is picked up by the first picking tool 6 (alternatively the second or another picking tool can be used for picking up an additional sample). Thus the controller 23 in this case controls the positioning of the transfer device 15 such that the second picking tool 7 is discarded as described above. Then (or simultaneously) the first picking tool 6 in the picking tool holder 9 of the positioning device 8 is lowered from the starting position above the culture dish 3 towards the culture dish and into contact with the microorganism 4 to pick up an additional sample of said microorganism. Thereafter the first picking tool 6 is automatically raised with the additional sample of the microorganism away from the culture dish to the transfer position. Then said transferring device automatically transfers the first picking tool with the additional sample of the microorganism from the transfer position of the positioning device 8 to a position above the suspension tube 11. The first picking tool 6 with the additional sample of the microorganism is lowered into the suspension medium 14 and is oscillated by the transferring device 15 in a linear vertical movement for a period of time for releasing the additional sample of said microorganism in the suspension medium. Again the turbidity is measured during the oscillation, and the measured value is compared with the first and second threshold value stored in the memory of the controller 23. In this case the controller 23 can be arranged for controlling the movement of the transferring device 15 such that the first picking tool 6 is raised to the waiting position if during oscillation the on-line measurement value of the turbidity performed by the turbidity meter 20 is equal to or lower than the first threshold value and equal to or greater than the second threshold value.

Suspension tubes which are particularly useful in the inventive apparatus have a substantially circular cross-section with a diameter of about 6 to about 12 mm, preferably about 10 mm. In these relatively small suspension tubes the controller 23 can control the automatic suspension medium dispenser 12 such that the supplied initial amount of suspension medium is about 0.5-2 ml, preferably about 1 ml.

The oscillation of the transferring device 15 is controlled by the controller 23 such that the picking tool oscillates at a frequency between about 5 Hz to about 120 Hz, preferably about 30 Hz to about 90 Hz, most preferably about 50 Hz, with an amplitude of about 0.5 mm to about 4 mm, preferably about 2 mm to about 3 mm. The controller is furthermore arranged for controlling the oscillation of the transferring device 15 such that the period of time during which the picking tool oscillates is about 3 seconds to about 10 seconds, preferably about 6 seconds.

The inventive apparatus 1 in addition comprises a conveyor 24 of which the end position can form the stage 2 for the culture dish or as shown in FIG. 1 a conveyor 24 and a stage 2 which are mutually positioned such that a culture disk can be transported onto the stage and removed from the stage by appropriate operation of the conveyor 24. The conveyor 24 is controlled by the controller 23 for automatically positioning and removing a culture dish comprising said microorganism on and from the stage, respectively. Please note that in other, not shown, embodiments different means for automatically positioning and removing a culture dish on and from the stage, respectively, can be used. In particular the controller 23 is arranged for allowing a culture dish to be automatically removed from the stage by the automatic culture dish positioning and removing device only after the signal that the suspension tube with the suspension can be removed from the suspension tube holder for further processing has been provided. This ensures that it is always possible to pick up an additional sample, if necessary.

As shown in FIG. 1 the inventive apparatus 1 further comprises an automatic suspension tube positioning and removing device 25 for automatically positioning and removing a suspension tube in and from the suspension tube holder, respectively. In the shown embodiment automatic suspension tube positioning and removing device 25 comprises grasping means 26 for releasably grasping a suspension tube 11'. Again, the controller 23 is arranged for being communicatively connected to the automatic suspension tube positioning and removing device 25, 26 for controlling the operation of the automatic suspension tube positioning and removing device, and for automatically positioning a suspension tube in the suspension tube holder. The controller 23 in particular is arranged for automatically removing a suspension tube holder from the suspension tube holder by the automatic suspension tube positioning and removing device 25, 26 only after the signal that the suspension tube with the suspension can be removed from the suspension tube holder for further processing has been provided. In the shown embodiment the automatic suspension tube positioning and removing device 25 is movable along the rail 18 independent of the movement of the transferring device 15. In the position indicated by C empty suspension tubes can be fetched and suspension tubes with a suspension medium containing a sufficient concentration of microorganism can be handed over to equipment for further processing, such as an incubator. Please note that the position C can for example be formed by a multitrack system which can lead the suspension tube positioning and removing device 25 and the transferring device 15 to different location at which different components are present or processes can be performed.

The sample suspension thus prepared is used for performing characterization or identification of the microorganisms using MALDI and optionally used for other analysis, such as AST. For identifying microorganisms using MALDI a drop of said sample suspension is obtained; and this drop is transferred onto said target plate. A drop can be obtained by using another picking tool which is held by the grasping means 17 and which is automatically lowered in the suspension. When this picking tool is raised out of the suspension a drop of suspension will stick on the tip of this picking tool, which can be transferred along the track to position B, where the picking tool with the drop is lowered until the drop contacts the depositing spot on the target plate, and at least a part of the drop will remain on the depositing spot after the picking tool has been raised away from the target plate. Alternatively a pipetting tool, to be described below, can be used to pick up an amount of suspension from the suspension tube, transfer this amount to position B and deposit a drop of suspension on the target plate. After a drop of suspension has been deposited on the target plate, and in particular when this drop has been allowed to dry, a drop of a MALDI matrix solution is automatically overlaid on the amount or portion of the sample deposited on the target plate. For performing other tests or another analysis a second drop of said sample suspension can be obtained in a similar way, and such a drop may be automatically transferred to and deposited on e.g. a test culture dish which is further transferring in an automated way for performing a susceptibility test or another additional analysis.

Each suspension tube comprises an unique identifying mark, which is stored together with the properties of the suspension with a link to the identity of the culture dish from which the selected colony of microorganisms was obtained in the memory of said central control computer for the purpose of amongst other things correctly and in a fast manner link the obtained results of analysis with the culture dish and colony pertaining to said results.

Although not shown in FIG. 1 an amount of suspension can be taken from the suspension in the suspension tube by means of a pipetting tool which can be automatically held and positioned by the grasping means (functioning as pipetting tool holder) 17 and transferring or positioning device 15 in the same manner as a picking tool. The positioning device 15 is arranged for positioning said pipetting tool in a starting position above the suspension tube and for automatically lowering and raising the pipetting tool into and out of the suspension and for positioning the pipetting tool in a transfer position, respectively. When the pipetting tool is lowered into the suspension in said suspension tube the pipetting tool is operated in a manner known per se (e.g. using sub pressure) to pick up an amount of suspension. Thereafter the pipetting tool with said amount of suspension is raised to the transfer position. For holding the amount the pipetting tool comprises a pressurizable chamber closed by a controlled valve. The pipetting tool is automatically transferred by the transferring device 15 to the position B above one of the depositing spots of the target plate. In this position the pipetting tool is lowered to a predefined distance above the target plate, after which the chamber is pressurized to a pressure in a range of about 0.5 bar to 1.1 bar. The valve is then opened for such a time that a drop of suspension with a volume in a range of about 0.5 to 3.0 µl is deposited on the depositing spot, in particular covering at most approximately half of said one of the depositing spots of the target plate. After the drop has been deposited the pipetting tool is raised from the target plate and can be transferred to position C where it can be discarded or cleaned for reuse.

The invention claimed is:

1. A method comprising:
   locating one or more colonies of microorganisms in a culture dish;
   positioning a first picking tool in a picking tool holder of a positioning device;
   obtaining, with the positioning device, a first sample of at least one of the located colonies of microorganisms for performing MALDI, in part, by: (a) positioning the first picking tool above one of the located colonies of microorganisms in the culture dish, (b) automatically lowering the first picking tool towards the culture dish and into contact with the one of the located colonies of microorganisms, and (c) automatically raising the first picking tool with the sample of the one of the located colonies of microorganisms away from the culture dish;
   depositing, with the positioning device, at least some of the first sample on at least one depositing spot of a target plate having a plurality of depositing spots, in part, by: (a) positioning the first picking tool above one of the depositing spots of the target plate, (b) lowering the first picking tool such that at least some of the first sample comes into contact with the target plate, and (c) raising the first picking tool from the target plate;
   obtaining, with the positioning device, a second sample of at least one of the located colonies of microorganisms for performing a susceptibility test, in part, by: (a) positioning the first picking tool or a second picking tool above one of the located colonies of microorganisms in the culture dish, wherein, if used, the second picking tool is previously positioned in the picking tool holder of the positioning device, (b) automatically lowering the first or second picking tool towards the culture dish and into contact with the one of the located colonies of microorganisms, and (c) automatically raising the first or second picking tool with the sample of the one of the located colonies of microorganisms away from the culture dish;
   depositing, with the positioning device, at least some of the second sample in a suspension tube containing a suspension medium, in part, by: (a) positioning the first or second picking tool above the suspension tube, (b) lowering the first or second picking tool such that at least some of the second sample is submerged in the suspension medium in the suspension tube, and (c) raising the first or second picking tool from the suspension tube;
   measuring the turbidity of a suspension in the suspension tube comprising the at least some of the second sample and the suspension medium; and
   when the measured turbidity is below a first threshold value and above a second threshold value, providing a signal that the suspension tube holding the suspension can be further processed, wherein the first threshold value is equal to or greater than the second threshold value.

2. The method of claim 1 further comprising:
when the measured turbidity is above the first threshold value, dispensing, with an automatic suspension medium dispenser, an additional amount of suspension medium into the suspension tube.

3. The method of claim 2 further comprising:
when the measured turbidity is below the second threshold value:
optionally positioning a third picking tool in the picking tool holder of the positioning device;
obtaining, with the positioning device, an additional amount of the second sample, in part, by: (a) positioning the first, second, or third picking tool above one of the located colonies of microorganisms in the culture dish, (b) automatically lowering the first, second, or third picking tool towards the culture dish and into contact with the one of the located colonies of microorganisms, and (c) automatically raising the first, second, or third picking tool with the sample of the one of the located colonies of microorganisms away from the culture dish; and
depositing, with the positioning device, at least some of the additional amount of the second sample in the suspension in the suspension tube, in part, by: (a) positioning the first, second, or third picking tool above the suspension tube, (b) lowering the first, second, or third picking tool such that at least some of the additional amount of the second sample is submerged in the suspension medium in the suspension tube, and (c) raising the first, second, or third picking tool from the suspension tube.

4. The method of claim 1 further comprising:
when a signal that the suspension tube holding the suspension can be further processed is provided, depositing, with the positioning device, at least some of the suspension in a test culture dish.

5. The method of claim 4 further comprising:
transferring the target plate with the at least some of the first sample to an apparatus for performing MALDI for identification of the first sample; and
transferring the test culture dish with the at least some of the suspension to an apparatus for performing a susceptibility test.

6. The method of claim 1 further comprising overlaying a drop of a MALDI matrix solution on the at least some of the first sample on the target plate.

7. The method of claim 1, wherein the step of locating the one or more colonies of microorganisms in the culture dish is performed, in part, by: (a) obtaining an initial image of the culture dish including all the colonies of microorganisms in the culture dish, (b) displaying the initial image on a display, and (c) manually selecting at least one colony of microorganisms in the initial image.

8. The method of claim 1, wherein the step of locating the one or more colonies of microorganisms in the culture dish is performed, in part, by: (a) obtaining an initial image of the culture dish including all the colonies of microorganisms in the culture dish, (b) positioning the culture dish on a stage comprising an imaging device, (c) obtaining an image of the culture dish, and (d) automatically identifying at least one colony of microorganisms by comparing the image obtained by the imaging device with the initial image of the culture dish.

9. The method of claim 1, wherein the at least some of the first sample is deposited on at most approximately half of the at least one of the depositing spots of the target plate.

10. The method of claim 1, wherein (a) the second picking tool is positioned in the picking tool holder of the positioning device, (b) the second sample is obtained with the second picking tool, not the first picking tool, and (c) the at least some of the second sample is deposited in the suspension tube with the second picking tool, not the first picking tool.

11. The method of claim 1, wherein (a) the second sample is obtained with the first picking tool, not the second picking tool and (b) the at least some of the second sample is deposited in the suspension tube with the first picking tool, not the second picking tool.

12. The method of claim 1, wherein the first and second samples comprise at least one of the same located colonies of microorganisms in the culture dish.

13. The method of claim 1, wherein the first and second samples consist entirely of a single one of the located colonies of microorganisms in the culture dish.

14. A system comprising:
a positioning device comprising a picking tool holder, wherein the picking tool holder is adapted to releasably engage a picking tool;
a turbidity meter; and
one or more processors communicatively coupled to the positioning device and the turbidity meter, wherein the one or more processors are arranged for automatically controlling (a) the movement of the positioning device and (b) the operation of the turbidity meter, and wherein the one or more processors are configured to:
obtain locations of one or more colonies of microorganisms in a culture dish;
control the positioning device to position a first picking tool in the picking tool holder;
control the positioning device to obtain a first sample of at least one of the located colonies of microorganisms in a culture dish, in part, by: (a) positioning the first picking tool above one of the located colonies of microorganisms in the culture dish, (b) automatically lowering the first picking tool towards the culture dish and into contact with the one of the located colonies of microorganisms, and (c) automatically raising the first picking tool with the sample of the one of the located colonies of microorganisms away from the culture dish;
control the positioning device to deposit at least some of the first sample on at least one depositing spot of a target plate having a plurality of depositing spots, in part, by: (a) positioning the first picking tool above one of the depositing spots of the target plate, (b) lowering the first picking tool such that at least some of the first sample comes into contact with the target plate, and (c) raising the first picking tool from the target plate;
control the positioning device to obtain a second sample of at least one of the located colonies of microorganisms in the culture dish, in part, by: (a) positioning the first picking tool or a second picking tool above one of the located colonies of microorganisms in the culture dish, wherein, if used, the second picking tool is previously positioned in the picking tool holder of the positioning device, (b) automatically lowering the first or second picking tool towards the culture dish and into contact with the one of the located colonies of microorganisms, and (c) automatically raising the first or second picking tool with the sample of the one of the located colonies of microorganisms away from the culture dish;

control the positioning device to deposit at least some of the second sample in a suspension tube containing a suspension medium, in part, by: (a) positioning the first or second picking tool above the suspension tube, (b) lowering the first or second picking tool such that at least some of the second sample is submerged in the suspension medium in the suspension tube, and (c) raising the first or second picking tool from the suspension tube;

control the turbidity meter to provide a measurement of the turbidity of a suspension in the suspension tube comprising the at least some of the second sample and the suspension medium; and when the provided measurement of the turbidity is below a first threshold value and above a second threshold value, provide a signal that the suspension tube holding the suspension can be further processed, wherein the first threshold value is equal to or greater than the second threshold value.

15. The system of claim 14 further comprising:

an automatic suspension medium dispenser communicatively coupled to the one or more processors, wherein the one or more processors are further arranged for automatically controlling the operation of the automatic suspension medium dispenser, and wherein the one or more processors are further configured to:
  when the provided measurement of the turbidity is above the first threshold value, control the automatic suspension medium dispenser to dispense an additional amount of suspension medium into the suspension tube.

16. The system of claim 14 further comprising:

a display communicatively coupled to the one or more processors, wherein the one or more processors are further arranged for automatically controlling the operation of the display, and wherein the one or more processors are configured to obtain the locations of the one or more colonies of microorganisms in the culture dish, in part, by: (a) obtaining an initial image of the culture dish including all the colonies of microorganisms in the culture dish, (b) controlling the display to display the initial image, and (c) receiving a manual selection of at least one colony of microorganisms in the initial image.

17. The system of claim 14 further comprising:

an imaging device communicatively coupled to the one or more processors, wherein the one or more processors are further arranged for automatically controlling the operation of the imaging device, and wherein the one or more processors are configured to automatically obtain the locations of the one or more colonies of microorganisms in the culture dish, in part, by: (a) obtaining an initial image of the culture dish including all the colonies of microorganisms in the culture dish, (b) controlling the imaging device to provide a second image of the culture dish, and (c) identifying at least one colony of microorganisms by comparing the second image with the initial image of the culture dish.

18. The system of claim 14, wherein the first and second samples comprise at least one of the same located colonies of microorganisms in the culture dish.

19. The system of claim 14, wherein the first and second samples consist entirely of a single one of the located colonies of microorganisms in the culture dish.

20. The system of claim 14, wherein the first and second picking tools are pipetting tools.

* * * * *